United States Patent [19]

Schroeppel

[11] Patent Number: 5,776,169
[45] Date of Patent: Jul. 7, 1998

[54] IMPLANTABLE CARDIAC STIMULATOR FOR MINIMALLY INVASIVE IMPLANTATION

[75] Inventor: Edward A. Schroeppel, Lake Jackson, Tex.

[73] Assignee: Sulzer Intermedics Inc., Angleton, Tex.

[21] Appl. No.: 847,915

[22] Filed: Apr. 28, 1997

[51] Int. Cl.[6] ............................................. A61N 1/36
[52] U.S. Cl. .................................................... 607/36
[58] Field of Search .............................. 607/36, 37, 9, 607/2, 5

[56] References Cited

PUBLICATIONS

Nicholas P. D. Smyth, *Pacemaker Implantation: Surgical Techniques*; Pacemaker Therapy, L. Dreifus, M.D., Editor pp. 35,40, 1983.

D.F. Morse et al., *A Guide to Cardiac Pacemakers, Defibrillators, and Related Products*, pp. 7-1 thru 7-62, 1991.

Phillip Varriale et al., *Cardiac Pacing: A Concise Guide to Clinical Practice*, 148-149, 1979.

*Primary Examiner*—Scott M. Getzow
*Attorney, Agent, or Firm*—John R. Merkling

[57] ABSTRACT

An implantable system is provided for subcutaneous surgical implantation. The implantable system includes a smoothly contoured casing and an implantable apparatus designed to perform a desired medical function, such as cardiac stimulation, diagnosis, or drug infusion. The casing includes a chamber for enclosing the implantable apparatus. The casing is provided with one end that is separated from a second, and opposing, end by a slit. The shape of the casing and the separated ends enables implantation via a shorter incision than is possible using a comparably sized conventional implantable device. Some examples of possible implantable apparatus include cardiac stimulators and sensors, or drug infusion pumps.

18 Claims, 3 Drawing Sheets

IMPLANTABLE CARDIAC STIMULATOR FOR MINIMALLY INVASIVE IMPLANTATION

BACKGROUND OF THE INVENTION

1. Field of the Invention

This invention relates generally to medical devices for subcutaneous implantation, and more particularly, to implantable cardiac stimulators.

2. Description of the Related Art

The advent of implantable devices, such as cardiac pacemakers, has brought welcome relief to those patients suffering from various forms of cardiac arrhythmia. Today, many different types of medical devices are implanted subcutaneously, such as cardiac stimulators and recorders, and implantable infusion pumps. The surgical techniques used to implant these devices have remained relatively constant over the past thirty years. For example, the implantation of most cardiac stimulators involves making an incision in the right pectoral region above the areola and forming a pocket in the subcutaneous tissue by blunt dissection. The device is then inserted through the incision and placed in the pocket. The incision is then closed by conventional suturing. The incision is normally linear and must be slightly longer than the smallest width of the device. For a circular device, that length corresponds roughly to the diameter of the implant. For a more highly elliptically shaped implant, the length will be the distance between the two sides of the implant taken at the midpoint of the implant. The length of the incision in excess of the width of the implanted device required will depend upon the thickness of the device to be implanted, as well as the elasticity of the patient's skin.

Early implantable devices, such as pacemakers, were rather large devices, sometimes requiring incisions in excess of 8 cm in length. Despite advances in the miniaturization of implantable devices that have generally tracked the increasing miniaturization of electronics, current implantable device designs still require a surgical incision that is long enough to accommodate the full extent of the smallest width presented by the particular device.

There are several disadvantages associated with conventional implantable devices. Because the surgical incision required to implant such conventional devices is still larger than the widths of the devices themselves, the surgical procedures yield less than satisfactory cosmetic results, and impose longer healing times. The cosmetic considerations may be most heightened in young patients, or in those patients where the device will only be implanted for a finite period of time, such as, for example an implantable diagnostic recorder that may have a life expectancy of one year or less.

The present invention is directed to overcoming or reducing one or more of the foregoing disadvantages.

SUMMARY OF THE INVENTION

In accordance with one aspect of the present invention, a casing for enclosing an apparatus to be implanted subcutaneously via an incision is provided. The casing includes a chamber for enclosing said apparatus, a first end, and a second end opposing the first end. The casing has a slit separating the first end from the second end such that the casing may be implanted by inserting one of the opposing ends into the incision and rotating the casing until the other of the opposing ends passes through the incision.

In accordance with another aspect of the present invention, an implantable system for subcutaneous placement via an incision is provided. The implantable system includes a casing that has a chamber and a slit that defines first and second opposing ends of the casing. The casing may be implanted by inserting one of the opposing ends into the incision and rotating the casing until the other of the opposing ends passes through the incision. An implantable apparatus is disposed within the chamber of the casing.

In accordance with still another aspect of the present invention, a cardiac stimulator for processing signals to or from a heart that is adapted for subcutaneous implantation via an incision is provided. The cardiac stimulator includes a casing that has a chamber and a slit that defines first and second opposing ends of the casing. Circuitry is disposed within the chamber for processing the signals. The cardiac stimulator is capable of implantation by inserting one of the opposing ends into the incision and rotating the casing until the other of the opposing ends passes through the incision.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
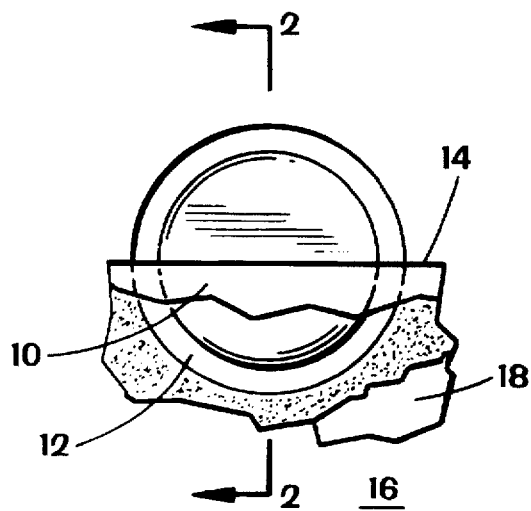
FIG. 1 is a top view of a conventional implantable device shown post implant.
Figure 2:
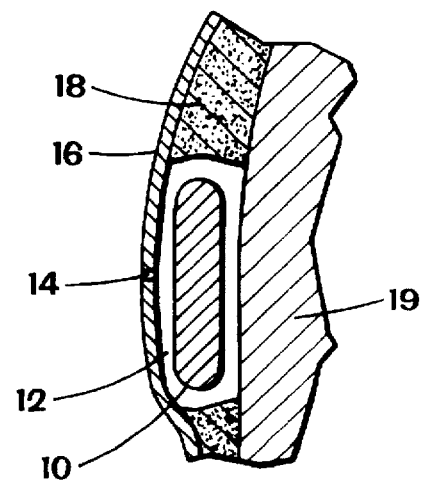
FIG. 2 is a sectional view of FIG. 1 at section 2—2.

Turning now to the drawings, and in particular to FIGS. 1 and 2, there is shown an exemplary conventional implantable device 10 after surgical subcutaneous implantation. In FIG. 1, a portion of the surrounding tissue is shown cut away to reveal the lower edge of the implantable device 10. The implantable device 10 is disposed in a circular pocket 12 that approximates the shape of the implantable device 10. The implantable device 10 is inserted into the pocket via an incision 14 which is made through all of the epidermis and derma layers 16 to expose the subcutaneous tissues 18. Because the skin and underlying tissue have limited elasticity, the incision 14 must normally be made slightly longer than the shortest width of the implanted device 10. After the incision 14 is made, the skin 16 is retracted and the pocket 12 is dissected using surgical instruments and/or gloved fingers. After the pocket 12 has been dissected, the implantable device 10 is inserted into the pocket 12 by retracting the skin 16 and inserting one half of the implantable device 10 past the incision 14 into the pocket 12 and advancing the implantable device 10 until the other half may be slipped through the incision 14 and into the pocket 12. The incision 14 is then closed by suturing or stapling. The device 10 is sandwiched between the skin 16 and the underlying muscle tissue 19.

Figure 3:
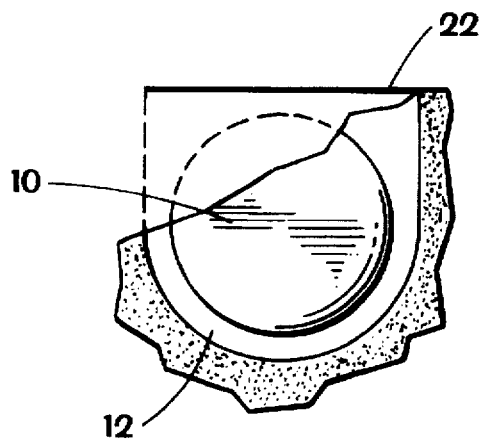
FIG. 3 is a top view of the conventional implantable device of FIG. 1 shown in a different variety of tissue pocket.

In a surgical variation for the implantable device 10 shown in FIGS. 1 and 2, the implantable device 10 may be disposed in a pocket 20 that is disposed to one side or the other of an incision 22 as shown in FIG. 3. This is in contrast to FIGS. 1 and 2 where the incision 14 is medially disposed.

Figure 4:
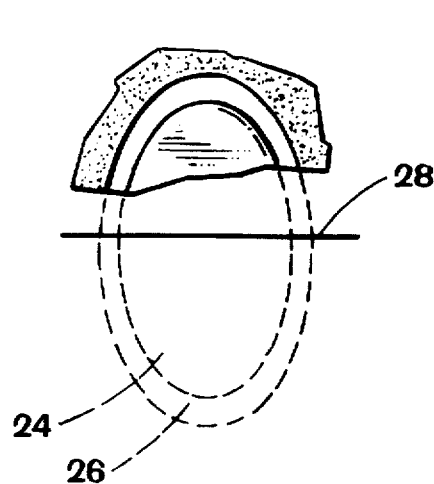
FIG. 4 is a top view of another variety of conventional implantable device shown post implant.
Figure 5:
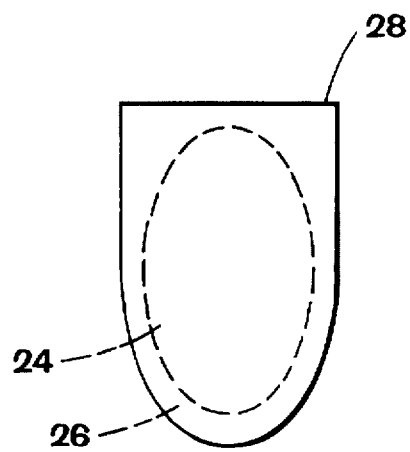
FIG. 5 is a top view of the conventional implantable device of FIG. 4 shown in a different variety of tissue pocket.
Figure 6:
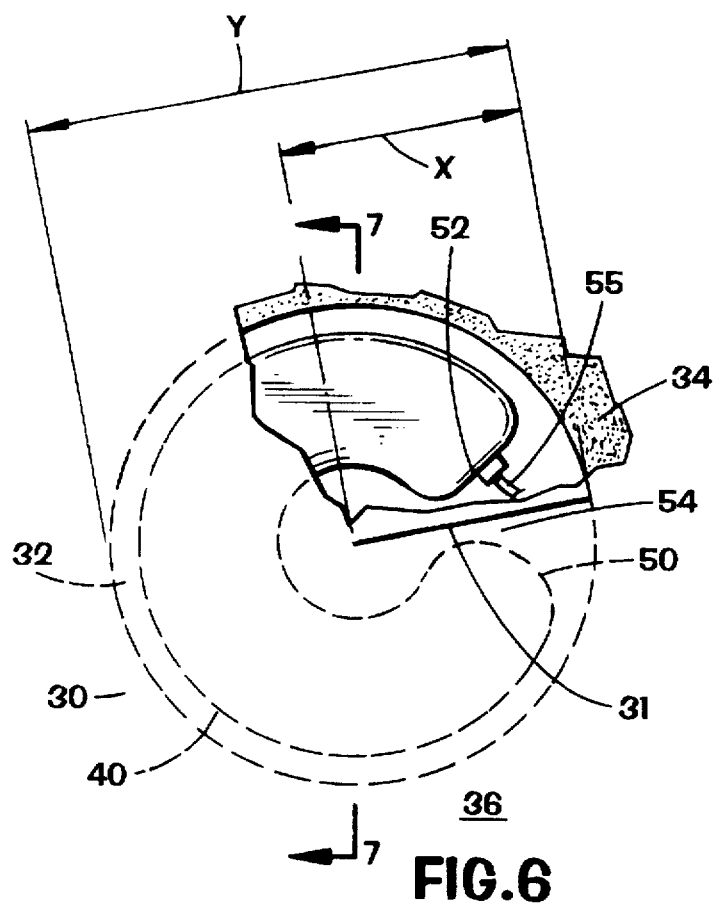
FIG. 6 is a top view of an implantable system in accordance with the present invention shown post implant.
Figure 7:
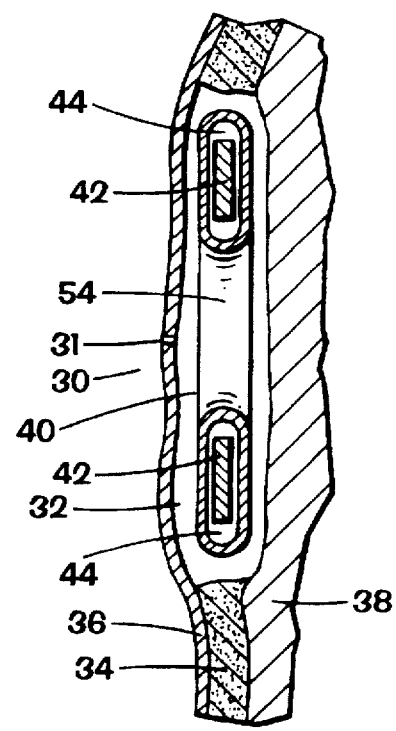
FIG. 7 is a sectional view of FIG. 6 taken at section 7—7.

Conventional implantable devices come in a variety of different geometries, though they typically present a generally rounded shape. However, the requirement for an incision that is longer than the smallest width of a conventional implantable device transcends the particular geometry of the implantable device. In this regard, FIGS. 4 and 5 depict a highly elliptical implantable device 24 disposed in pockets of the type shown, respectively, in FIGS. 1 and 3, but with pocket dissections to accommodate a more highly elliptical implantable device 24. The incision must be sized larger than the full extent of the smallest width presented by the device 24. Referring now to FIGS. 6 and 7, therein is depicted an exemplary embodiment of an implantable system 30 in accordance with the present invention. The system 30 is shown surgically implanted via an incision 31, and is disposed in a pocket 32 dissected from the subcutaneous tissue 34 between the epidermis and derma layers 36 and the underlying muscular tissue 38. The implantable system 30 includes a smoothly contoured casing 40 and an implantable apparatus 42. The casing 40 has a chamber 44 for enclosing the implantable apparatus 42. The casing 40 is provided with one end 50 that is separated from a second, and opposing, end 52 by a slit 54. The slit 54 may be uniformly shaped, or take on a bulbous shape as shown in FIGS. 6 and 7. The shape of the casing 40 and the separated ends 50 and 52 enables implantation by inserting one end 50 or 52 of the casing 40 into the pocket 32 via the incision 31, and then rotating the casing 40 until the other end passes through the incision 31. At least one, and possibly both, of the ends 50 and 52 should be rounded to facilitate easy insertion into the incision 31 and smooth movement in the pocket 32.

The casing 40 has a generally elliptical outline when viewed from above, and has an overall generally toroidal shape. However, the skilled artisan will appreciate that the outline and cross-section of the casing 40 may be varied greatly, subject to the general design goals of keeping the casing 40 relatively thin to minimize skin bulging, and avoiding sharp corners or edges which may damage tissue. The shape of the casing 40 and the separated ends 50 and 52 enables implantation via a shorter incision than is possible using a comparably sized conventional implantable device. The dimension X represents the length of the incision 31 necessary to implant the implantable system 30. In contrast, the dimension Y represents the required length for an incision to implant a comparably sized conventional implantable device.

The casing 40 is preferably fabricated from a biocompatible material that provides a degree of rigidity sufficient to protect the implantable apparatus 42 enclosed therein. Examples of suitable materials include titanium, stainless steel, or similar materials.

The implantable apparatus 42 performs a desired medical function, such as cardiac stimulation or diagnosis, or drug infusion. Some examples of possible implantable apparatus 42 include cardiac stimulators and sensors, or drug infusion pumps. The implantable apparatus 42 may be connected to other parts of the body via a lead or catheter 55, as necessary.

Figure 8:
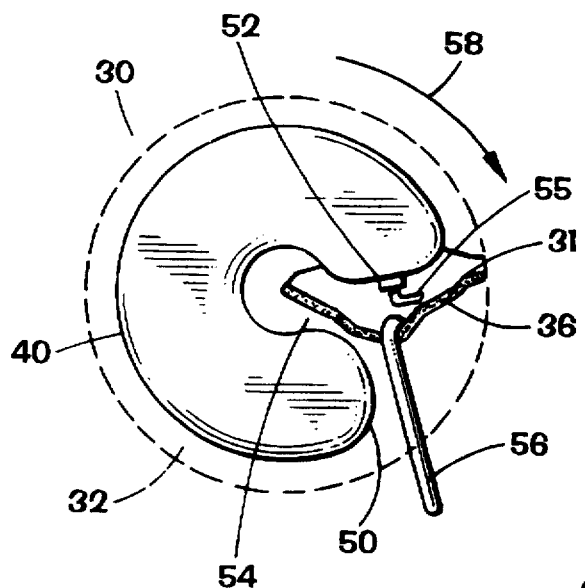
FIG. 8 is a top view of the implantable system of FIG. 6 just prior to surgical insertion into a tissue pocket.
Figure 9:
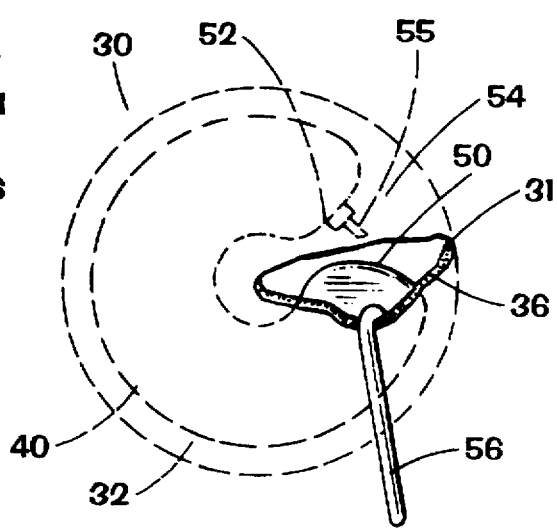
FIG. 9 is a top view of the implantable system of FIG. 6 just after insertion into a tissue pocket.

The procedure for implanting the implantable system 30 may be understood by reference to FIGS. 8 and 9. The incision 31 is made and retracted using a retractor 56, as shown, or by hand. The pocket 32 is then dissected to conform to the general shape of the casing 40. It is anticipated that since the incision 31 is shorter than the incisions made for conventional implantable devices, there will be less room for the surgeon to do the bulk of the dissection using gloved fingers. Accordingly, a larger percentage of the pocket dissection may have to be accomplished using surgical instruments. After the pocket 32 is dissected, the end 52 of the casing 40 is slipped into the incision 31 beneath the retracted skin layers 36. The casing 40 is then rotated in the direction of the arrow 58 until the end 50 of the casing 40 slips though the incision 31 and into the pocket 32 as shown in FIG. 9. After the casing 40 is fully disposed in the pocket 32, any necessary leads or catheters 55 may be attached and/or positioned, as necessary, and the incision 31 may be closed by suturing or stapling. Since the epidermis and derma layers 36 protrude into the slit 54 during implantation, the slit 54 should be sized to accommodate the maximum width anticipated for those layers 36.

It is anticipated that, because some available storage volume of the casing 40 is given up in order to accommodate the slit 54, the overall diameter of a given casing 40 will have to be increased slightly to provide a storage volume for circuitry or other devices that is comparable to a comparably sized conventional implant design. This will result in a slightly larger pocket 32. However, it is anticipated that keeping the largest width of the slit 54 relatively small in relation to the overall size of the casing 40, will require only a rather small increase in the overall diameter of the casing 40.

The implantation procedure may be varied to achieve a different final orientation of the implantable system 30. For example, referring again to FIGS. 8 and 9, the end 50 of the casing 40 could have been inserted first and the casing 40 rotated in the direction opposite to the arrow 58 to achieve a final orientation of the casing 40 that is directly opposite of that shown in FIG. 9.

Figure 10:
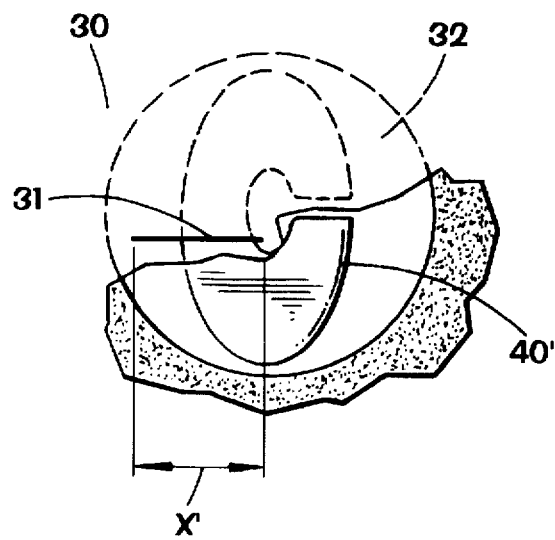
FIG. 10 is a top view of an alternate embodiment of an implantable system in accordance with the present invention.
Figure 11:
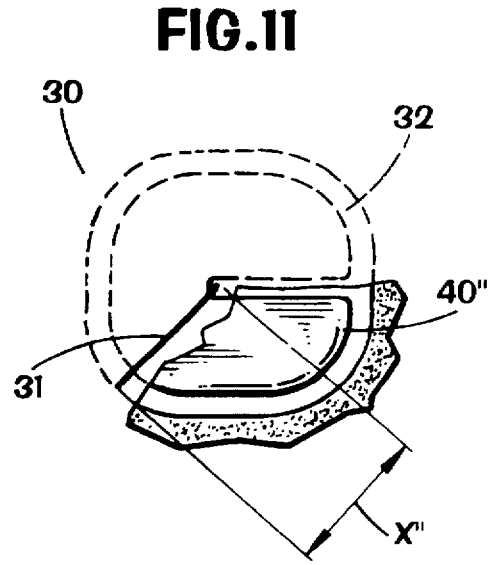
FIG. 11 is a top view of another alternate embodiment of an implantable system in accordance with the present invention.

As noted above, the basic concept of utilizing the slit 54 to separate the two opposing ends 50 and 52 of the casing 40 may be applied to a variety of different geometrical shapes for the casing 40. For example, a casing 40' may be highly elliptically shaped as shown in FIG. 10, or semi-rectangularly shaped as in FIG. 11. The length of the incision 31 necessary to accommodate a particularly shaped casing will normally be slightly greater than the largest width which must pass through the incision 31. For example, in FIG. 10, the casing 40' is highly elliptical and the corresponding minimum incision length will be approximated by the distance X'. Similarly, with regard to the semi-rectangularly shaped casing 40" shown in FIG. 11, the minimum incision length will be approximately the distance X".

Figure 12:
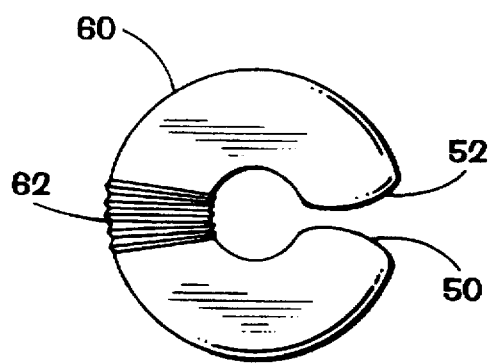
FIG. 12 is a top view of another embodiment of an implantable system in accordance with the present invention.
Figure 13:
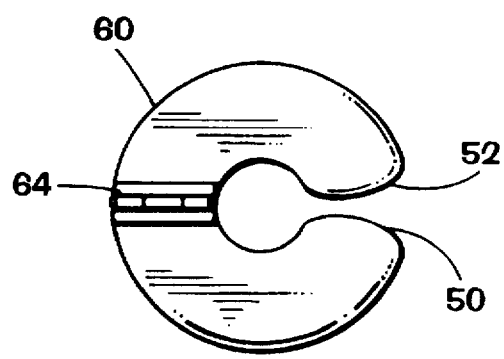
FIG. 13 is a top view of another embodiment of an implantable system in accordance with the present invention.

In some circumstances, a deeper than usual implant pocket may be medically indicated. Deeper implant depths may be accomplished using any of the aforementioned embodiments by fabricating a casing with a wider slit to accommodate a thicker layer of skin and underlying tissue. However, this approach may reduce the available storage volume in the casing chamber if the thickness of the casing is not increased. Alternatively, the casing may be modified so that the ends of the casing may move vertically relative to each other, to achieve, in effect, a widened slit without a loss of storage volume. This modification may be accomplished in a variety of ways. Using the embodiment shown in FIGS. 6 and 7 as an example, the casing 40 may be fabricated from a flexible material so that one end 50 may be bent away from the patient and the other end 52 may be bent towards the patient, or vice versa. The flexible material is preferably a biocompatible plastic. Referring to FIGS. 12 and 13, the relative pivoting movement of the ends 50 and 52 may alternatively be achieved by providing a casing 60 with a bellows-like hinge 62 as shown in FIG. 12, or a pinned hinge 64 as shown in FIG. 13. Any wires or plumbing in the casing may be channeled directly through the hinge 62 or through a conduit (not shown) disposed on the back side of the hinge 64.

The skilled artisan will appreciate that use of the foregoing embodiments will provide a significantly less invasive implant capability. The wounds produced should heal faster and yield a more cosmetically desirable post-surgical appearance for the patient.

While the invention may be susceptible to various modifications and alternative forms, specific embodiments shown by way of example in the drawings have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A casing for enclosing an apparatus to be implanted subcutaneously via an incision, comprising:

a chamber for enclosing said apparatus;

a first end; and a second end opposing said first end;

said casing having a slit separating said first end from said second end, such that said casing may be implanted by inserting one of said opposing ends into said incision and rotating said casing until the other of said opposing ends passes through said incision.

2. The casing of claim 1, wherein said casing is elliptically shaped.

3. The casing of claim 1, wherein said casing is toroidally shaped.

4. The casing of claim 1, wherein said casing is fabricated from a flexible material such that one of said opposing ends may be moved vertically relative to the other of said opposing ends.

5. The casing of claim 1, comprising a hinge coupled to said casing to enable one of said opposing ends to move vertically relative to the other of said opposing ends.

6. An implantable system for subcutaneous placement via an incision, comprising:

a casing having a chamber, and a slit defining first and second opposing ends of said casing, such that said casing may be implanted by inserting one of said opposing ends into said incision and rotating said casing until the other of said opposing ends passes through said incision; and an implantable apparatus disposed within said chamber.

7. The implantable system of claim 6, wherein said casing is elliptically shaped.

8. The implantable system of claim 6, wherein said casing is toroidally shaped.

9. The implantable system of claim 6, wherein said casing is fabricated from a flexible material such that one of said opposing ends may be moved vertically relative to the other of said opposing ends.

10. The implantable system of claim 6, comprising a hinge coupled to said casing to enable one of said opposing ends to move vertically relative to the other of said opposing ends.

11. The implantable system of claim 6, wherein said apparatus comprises a cardiac stimulator.

12. The implantable system of claim 6, wherein said apparatus comprises a cardiac sensor.

13. The implantable system of claim 6, wherein said apparatus comprises an implantable infusion pump.

14. A cardiac stimulator for processing signals to or from a heart and being adapted for subcutaneous implantation via an incision, comprising:

a casing having a chamber and a slit defining first and second opposing ends of said casing; and circuitry disposed within said chamber for processing said signals, said cardiac stimulator being capable of implantation by inserting one of said opposing ends into said incision and rotating said casing until the other of said opposing ends passes through said incision.

15. The cardiac stimulator of claim 14, wherein said casing is elliptically shaped.

16. The cardiac stimulator of claim 14, wherein said casing is toroidally shaped.

17. The cardiac stimulator of claim 14, wherein said casing is fabricated from a flexible material such that one of said opposing ends may be moved vertically relative to the other of said opposing ends.

18. The cardiac stimulator of claim 14, comprising a hinge coupled to said casing to enable one of said opposing ends to move vertically relative to the other of said opposing ends.

* * * * *